United States Patent [19]

Dadoo et al.

[11] Patent Number: 5,310,463

[45] Date of Patent: May 10, 1994

[54] ON-COLUMN JUNCTION FOR CAPILLARY COLUMNS

[75] Inventors: Rajeev Dadoo, Stanford; Luis A. Colòn, Menlo Park; Harvey A. Fishman, Stanford; Jason B. Shear, Menlo Park; Richard N. Zare, Stanford, all of Calif.

[73] Assignee: Board of Trustees of the Leland Stanford Junior University, Stanford, Calif.

[21] Appl. No.: 975,850

[22] Filed: Nov. 13, 1992

[51] Int. Cl.$^5$ .................... G01N 27/26; G01N 27/447
[52] U.S. Cl. ............................. 204/180.1; 204/299 R; 73/61.58; 73/61.53
[58] Field of Search .................. 204/299 R, 180.1; 210/198.2, 656; 73/61.58, 61.56, 61.55, 61.53, 61.52

[56] References Cited

U.S. PATENT DOCUMENTS

| | | | |
|---|---|---|---|
| 4,394,263 | 7/1983 | Dosch et al. | 210/198.2 |
| 4,837,161 | 6/1989 | Stevens et al. | 210/198.2 X |
| 5,073,239 | 12/1991 | Hjerten | 204/180.1 |
| 5,110,431 | 5/1992 | Moring | 204/180.1 |

FOREIGN PATENT DOCUMENTS 03-144361  6/1991  Japan ...................... 204/198.2

OTHER PUBLICATIONS

Stephen L. Pentoney, Jr. et al "On-line Connector for Microcolumns: Application to the On-Column o-Phthaldialdehyde Derivatization of Amino Acids Separated by Capillary Zone Electrophoresis" Analytical Chemistry vol. 60, No. 23(1988) 2625-2629.

"Coupled Fused Silica Capillaries for Rapid Capillary Zone Electrophoresis of Proteins," by Nashabeh et al., *Journ. of High Res. Chromatogr.*, 15:289-292 (May 1992).

"Post-Capillary Fluorescence Detection in Capillary Zone Electrophoresis," by Rose, Jr. et al., *Journ. of Chromatogr.*, 447:117-131 (1988).

"Fluorescence Detection in Capillary Electrophoresis: Evaluation of Derivatizing Reagents and Techniques," by Albin et al., *American. Chem. Soc.*, 63(5):417-422 (Mar. 1, 1991).

"On-Column Connector for Microcolumns: Application to the o-Phthaldialdehyde Derivatization of Amino Acids . . . ," by Pentoney, Jr., et al., *American Chem. Soc.*, 60(23):2625-2629 (Dec. 1, 1988).

"Direct Control of the Electroosmosis in Capillary Zone Electrophoresis . . . ," by Lee, et al., *American Chem. Soc.*, 62:1550-1552 (Jul. 15, 1990).

"Factors Affecting Direct Control of Electroosmosis Using an External . . . ," by Lee et al., *American Chem. Soc.*, 63:1519-1523 (Aug. 1, 1991).

"Electroosmotic Flow Control and Monitoring with an Applied Radial . . . ," by Hayes et al., *American Chem. Soc.*, 64:512-516 (Mar. 1, 1992).

"On-Column Sample Concentration Using Field Amplification in CZE," by Chien et al., *Anal. Chem.*, 64(8):489-496 (Apr. 15, 1992).

Article entitled "Capillary-Zone Electrophoresis with Fraction Collection . . . ," by Takigiku et al., *CZE for Desorption MS*.

*Primary Examiner*—John Niebling
*Assistant Examiner*—John S. Starsiak, Jr.
*Attorney, Agent, or Firm*—Majestic, Parsons, Siebert & Hsue

[57] ABSTRACT

An electrophoretic or chromatographic separation capillary containing a fluid defines a bore therein through which a sample travels and separates into components. The tube has a side wall defining a through hole therein which is surrounded by a medium including a substance. The substance is introduced into the capillary through the hole by means of gravity, pressure or electroosmosis. The substance introduced may be used to label sample components to enhance detection, or to enhance separation of sample components.

29 Claims, 5 Drawing Sheets

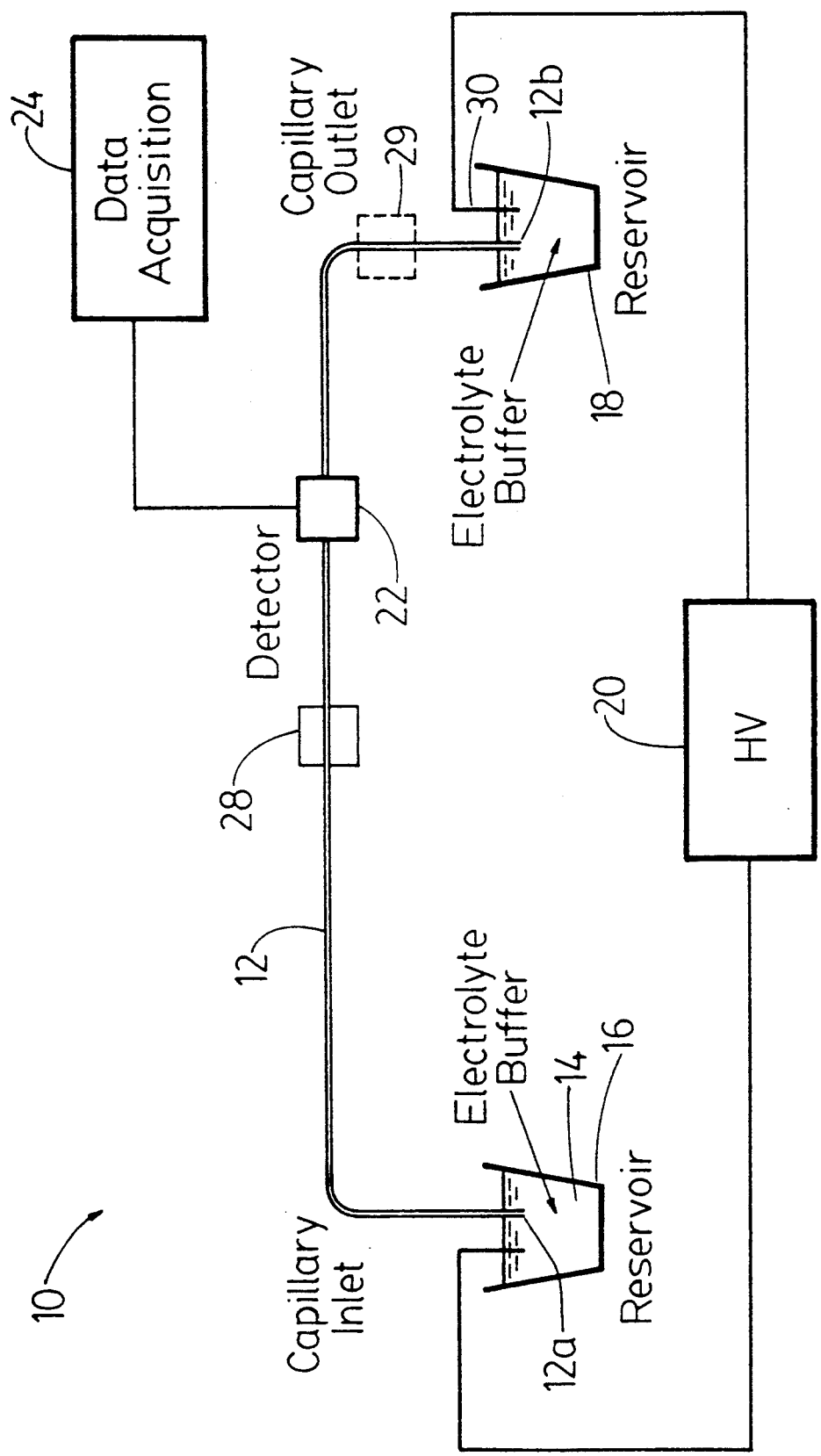
FIG._1.

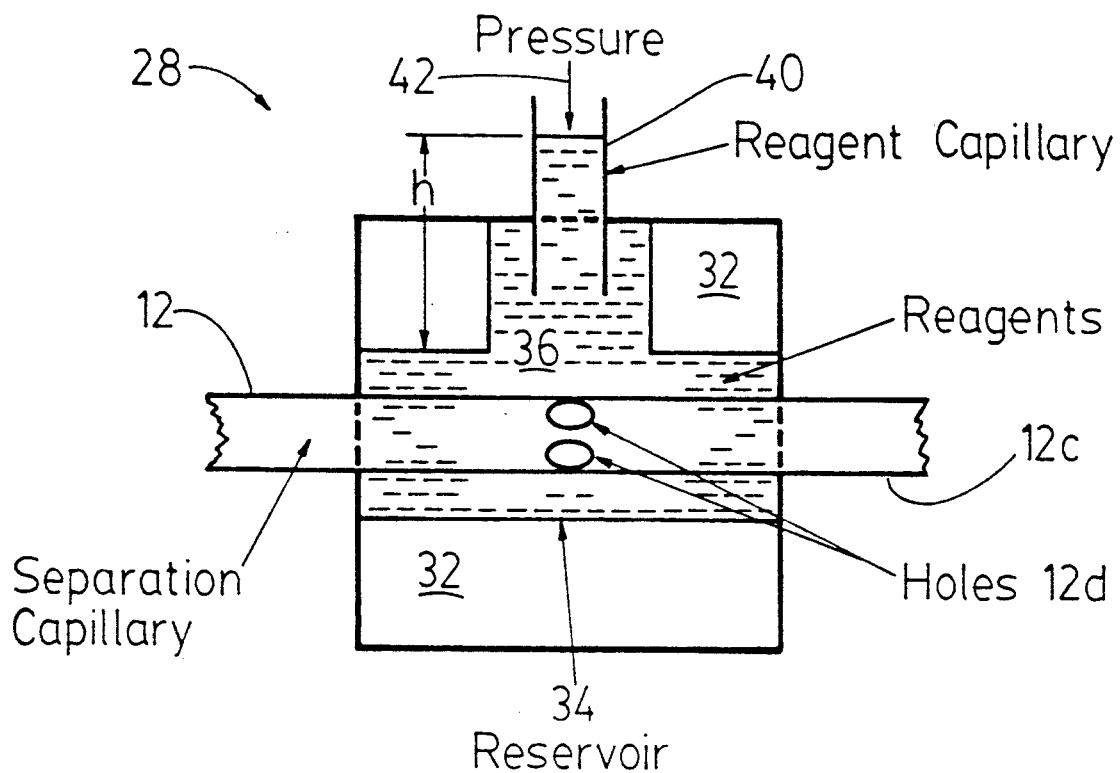
FIG._2.
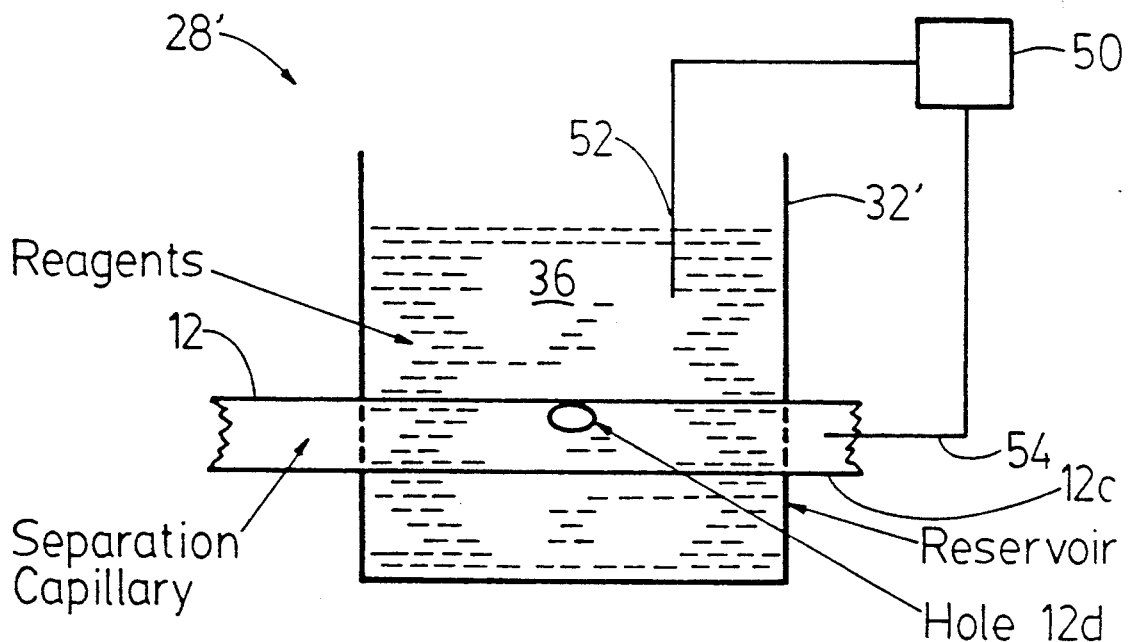
FIG._3.

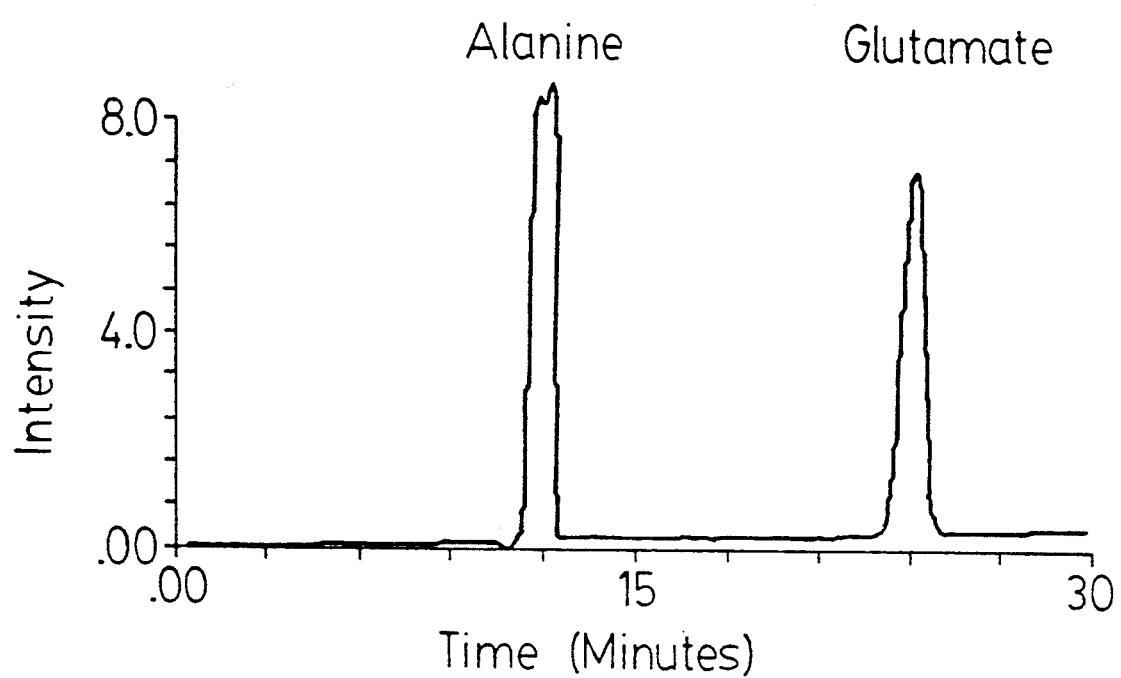
FIG._4.

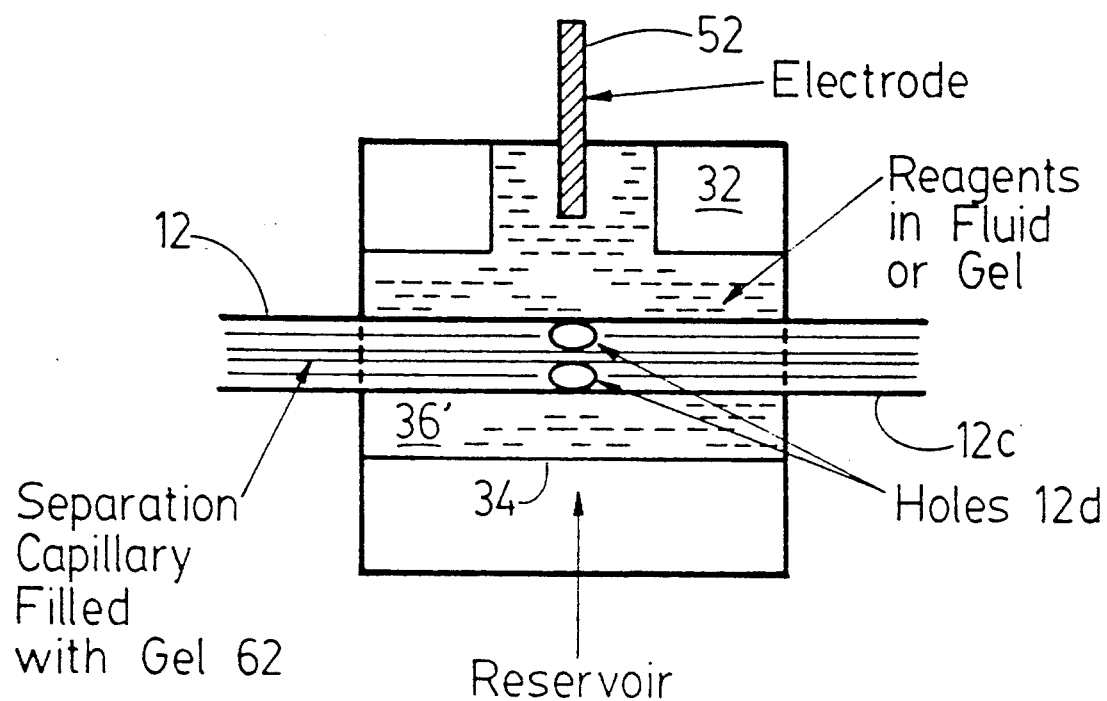
FIG._5A.
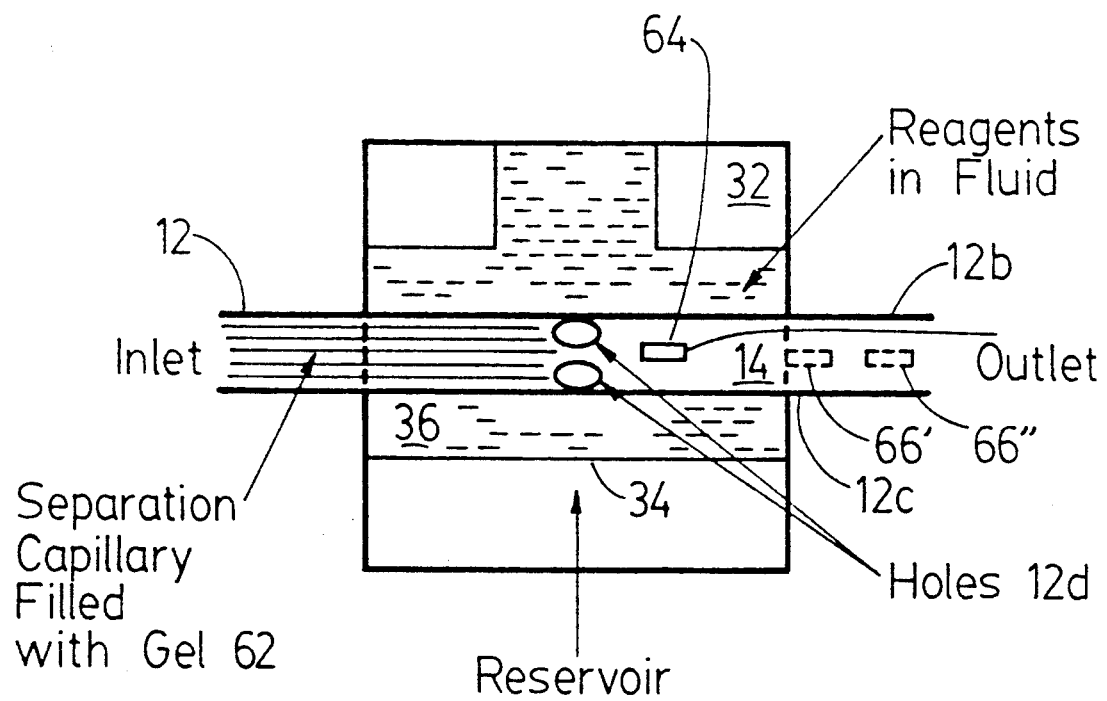
FIG._5B.

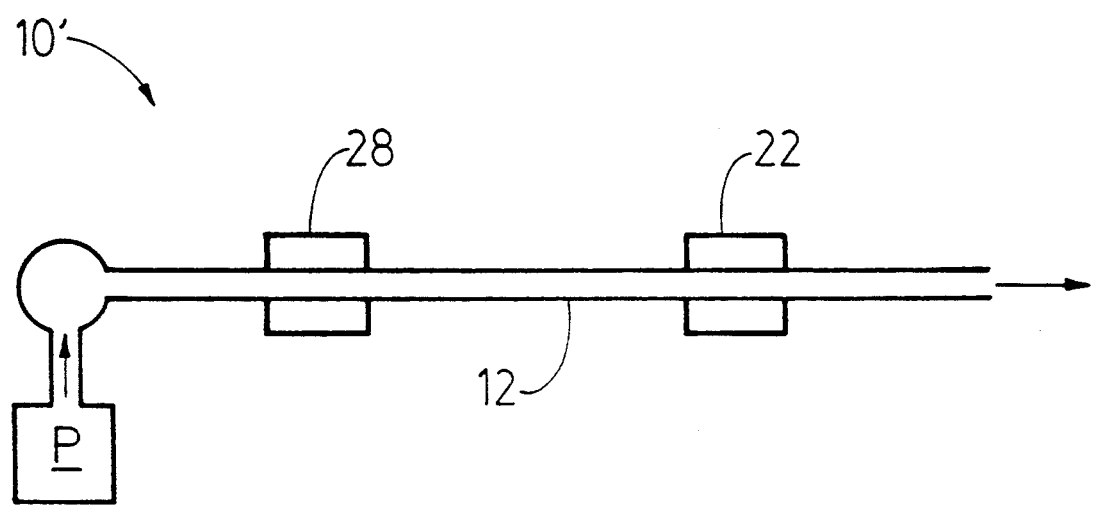
FIG._6.

ON-COLUMN JUNCTION FOR CAPILLARY COLUMNS

BACKGROUND OF THE INVENTION

This invention relates in general to separation systems and, in particular, to an on-column junction for capillary columns and method for introducing substances into the capillary columns.

Capillary separation techniques such as capillary electrophoresis (CE) involving gel or liquid columns, and capillary liquid and gas chromatography have become important analytical techniques for the analysis of various complex sample mixtures. The sample mixtures analyzed are typically in tiny volumes, such as a few nanoliters. Hence, a key factor in such techniques is the development of suitable detection schemes for detecting very small amounts of the sample components. A number of detection methods have been in use. These include absorbance, fluorescence, chemiluminescence, electrochemical, radioactivity, and mass spectrometric detection. In each of these procedures, it may be advantageous to attach to the analytes a label or tag, or add components to the mobile phase, that aid in the separation/detection of the species of sample components.

Various connectors have been proposed for introducing substances into the capillary columns. Two such connectors introduce labels or tags post-column. See Rose, Jr. et al., *J. Chromatoqr.*, Vol. 447, page 117 (1988); and Albin et al., *Anal. Chem.*, Vol. 63, page 417 (1991). Post-column derivatization, however, results in peak broadening and dilution of the separated sample components and requires careful alignment of capillaries. All conventional connection schemes employ a connector to connect one or more side tubes to a main capillary, where the connector may be a separate or an integral part of the main tube and/or side tube. Another connector for introducing a substance is described in Pentoney et al., *Anal. Chem.*, Vol. 60, page 2625 (1988), in which a T- or cross-shaped connector is proposed for introducing a substance into the capillary column prior to detection. Such a T-shaped or cross-shaped connector, however, requires that a tiny side capillary be connected to a hole drilled in the main separation capillary. Such alignment and connection process may be time-consuming and difficult to perform. It is therefore desirable to provide an alternative structure for introducing the substance such as a labeling reagent into the separation column.

SUMMARY OF THE INVENTION

The above-described difficulties are solved in the invention by employing a separation capillary tube with a through hole in the side wall, by surrounding the hole with a fluid medium containing a substance and by introducing the substance into the separation capillary through the hole, without any side tube at the hole for introducing the substance. The substance can, for example, be a labeling reagent.

Thus, one aspect of the invention is directed towards an apparatus for use in separating a sample into its components comprising a capillary tube defining a separation channel therein through which the sample travels and separates into its components, said tube having a side wall defining at least one hole therein. The apparatus further comprises a fluid medium surrounding the hole, where the hole extends through the side wall, thereby permitting a fluid or particles to pass between the channel in the capillary and the medium through the hole. The fluid medium contains a substance. The apparatus also includes means for introducing the substance into the channel through the hole.

Another aspect of the invention is directed towards a method for separating a sample into its components employing the capillary tube defined above. The method comprises introducing a sample into the tube and causing the sample to travel through the tube towards the location of the hole. The method further comprises surrounding the hole with a fluid medium containing a substance, introducing the substance into the channel through the hole and detecting the separated sample components at a location upstream or downstream from the hole.

BRIEF DESCRIPTION OF THE DRAWINGS

FIG. 1 is a schematic view of a capillary electrophoretic system useful for illustrating the invention.

FIG. 2 is a schematic view of a section of the separation capillary and a system for introducing a substance into the separation capillary of FIG. 1 to illustrate a first embodiment of the invention.

FIG. 3 is a schematic view of a section of the separation capillary and a system for introducing a substance into the separation capillary to illustrate a second embodiment of the invention.

FIG. 4 is an electropherogram obtained in on-column derivatization of alanine and glutamate with NDA using the system in FIGS. 1 and 2.

FIG. 5A is a schematic view of a section of the separation capillary and a system for introducing a substance into the separation capillary to illustrate a third embodiment of the invention.

FIG. 5B is a schematic view of a section of the separation capillary and a system for introducing a substance into the separation capillary to illustrate a fourth embodiment of the invention.

FIG. 6 is a schematic view of a capillary chromatographic system to illustrate the invention.

DETAILED DESCRIPTION OF THE PREFERRED EMBODIMENTS

FIG. 1 is a schematic system useful for illustrating the electrophoretic system useful for illuminating the invention. As shown in FIG. 1, apparatus 10 includes a capillary tube 12 with an inlet end 12a and an outlet end 12b. An electrolyte buffer 14 is supplied to the tube to end 12a from a reservoir 16. The electrolyte buffer which exits from outlet end 12b is collected in reservoir 18. A high voltage is applied between the two reservoirs, causing the electrolyte to move from reservoir 16 through inlet end 12a, capillary tube 12, and end 12b to exit in the reservoir 18. The high voltage is applied by a voltage supply 20. As is known in conventional capillary electrophoresis, a sample is introduced into the inlet end 12a, such as by dipping end 12a for a short time into a sample and applying a voltage across the tube to move a small portion of the sample into the tube. The end 12a is then dipped in the reservoir 16, where the portion of the sample is then carried under the influence of the electric field through tube 12 towards end 12b. As is also known in the electrophoretic art, different components of the sample may travel with different speeds in tube 12, causing the components to separate along the length of the tube. The actual rate of travel of each of the components is the sum of the electroosmotic flow rate of the fluid medium in the capillary and the electrophoretic migration rate of such component. These components are detected by detector 22 when the components pass the detector. Signals from detector 22 are sent to a data acquisition system 24 for analysis and recording.

In order to affect the detection of the sample components such as by altering the fluorescent characteristics of the sample, one or more holes (not shown in FIG. 1) are provided in capillary tube 12, as well as a system 28 (shown also in dotted line position 29 in FIG. 1 for reasons explained below) illustrated in more detail in FIG. 2 in the first embodiment. As shown in FIG. 2, the separation capillary 12 has a side wall 12c defining two through holes 12d therein. The through holes 12d have dimensions on the order of the internal cross-sectional dimensions of the separation capillary 12, which may range from 5 to 200 microns or higher. In the preferred embodiment, the holes 12d have diameters of the order of 20 microns, although the dimensions of the holes may range from 1 to 200 microns. A section of the separation capillary 12 is enclosed by a housing 32 defining a reservoir 34 therein for holding a fluid 36 which surrounds the holes 12d. The fluid 36 contains a substance or reagent which is to be introduced into the capillary 12. For convenience in description, identical components in this application are labeled by the same numerals.

The substance or reagent which is to be introduced into the capillary 12 may be introduced by a number of mechanisms, including gravity, pressure or electroosmosis. This is illustrated in FIG. 2, where the level of the reagent in a reagent capillary 40 is raised to height h above the level of capillary 12, so that the hydrostatic pressure would cause the reagents in reservoir 34 to enter capillary 12 through holes 12d.

As shown in FIG. 2, between housing 32 and capillary 12 at the two ends of the housing are two annular spaces therebetween. These spaces may be sealed by means of epoxy or other sealants or, alternatively, they may be sealed using a screw plug type mechanism known to those skilled in the art. The annular space between housing 32 and capillary 40 may be sealed in a similar manner. The reagent in the reservoir 34 may then be replenished through capillary 40. Instead of using gravity injection as explined above in reference to FIG. 2, the reagents may also be introduced into the capillary 12 by pressure, such as by applying pressure through capillary 40 so that the pressure in capillary 40 and reservoir 34 is at a higher pressure than that within capillary 12. This is illustrated symbolically by the arrow 42 in FIG. 2.

FIG. 3 is a schematic view of a system for introducing a substance into a separation capillary to illustrate a second embodiment of the invention. The side wall 12c of capillary 12 has only one hole 12d instead of two as in FIG. 2. It will be understood, however, that side wall 12c may define therein more than one or two holes for introduction of the reagent. Housing 32' encloses a reservoir for holding a reagent 36. In addition to gravity and pressure, the reagent may be introduced into the capillary 12 by means of electroosmosis, such as by applying a voltage between the reagent in the reservoir and one end of the capillary 12, such as by using voltage supply 50 through an electrode 52 dipped in reagent 36 in the reservoir and another electrode 54 electrically connected to the contents in tube 12, such as by being connected to electrode 30 of FIG. 1 for convenience. The potential difference between electrodes 52, 54 will cause reagent 36 to enter capillary 12 through hole 12d. As illustrated in FIG. 1, holes 12d and the system for introducing a substance into the capillary may be located upstream from detector 22 at solid line position 28. When system 28 is in such position, the reagent may be used to label or tag the sample components prior to their detection. The derivatization dye may be of the type that will migrate in a direction opposite to the analytes of interest under the influence of an electric field to extend the applicability of on-column detection with on-column derivatization in CE. Such applications are used both in fluid-filled columns as well as gel-filled columns.

FIG. 4 is a graphical illustration of an electropherogram showing the results of on-column derivatization of alanine ($100 \times 10^{-6}$M) and glutamate ($50 \times 10^{-6}$M) with NDA (0.13 mM) using the junction of FIG. 2 in a system shown in FIG. 1. The separation capillary 12 has an internal diameter of 0.1 mm and the length of 56 cm. The reagent capillary 40 has an internal diameter of 0.15 mm and a length of 90 cm. The high voltage supply 20 applies 11 kV across reservoirs 16, 18. The electrolyte used is a borate buffer (pH 8.7)+0.1 mM $CN^-$. System 28 encloses a section of the capillary 12 at a location which is 40 cm from the inlet end 12a. The reagent capillary reservoir was placed 9 cm above the separation buffer reservoirs 16, 18 and carried NDA dissolved in 1:1 buffer/methanol. The detection scheme used in detector 22 in this instance is laser induced fluorescence, using laser excitation at a wavelength of 454 nm and detecting the resulting fluorescence. Sample was injected for five seconds by gravity at a height of 7 cm above buffer reservoirs.

In addition to on-column derivatization, the system for introducing a substance into the capillary may also be used for four additional applications:
(1) Addition of enhancers of separation (e.g., micelles, organic modifiers, etc.) to the capillary column;
(2) Changing pH, concentration of mobile phase constituents, etc., to do gradient elution work;
(3) Grounding of the capillary (in CE) to aid post-column detection methods such as electrochemical and mass spectrometric;
(4) Inducing a reaction (e.g., chemiluminescence) at the junction by bringing in reagents not present otherwise.

The above applications may be applied with a system 28 placed as shown in FIG. 1 in an on-column detection system. It will be understood, however, that the above applications of the invention are applicable even where the detection is performed post-column.

Where the substance introduced would adversely affect the separation, analysis or detection of the sample, it may be desirable to introduce the substance after such separation, analysis or detection has been completed. Thus, instead of being at location 28 as shown in solid line in FIG. 1, the systems for introducing the substance such as that shown in FIGS. 2 and 3 and described above may instead be employed at dotted position 29 shown in dotted lines in FIG. 1. When it is introduced at such location, the substance introduced would merely flow or migrate through the section of the capillary tube 12 between location 29 and end 12b, thereby not interfering with the separation, analysis or detection of the sample in capillary 12 upstream from location 29.

The above-described scheme for introducing a substance into the capillary column may also be applied to capillary gel electrophoresis as illustrated in FIGS. 5A, 5B. FIG. 5A is a schematic view of a section of the above-described separation capillary 12 and a system for introducing a substance into the separation capillary to illustrate a third embodiment of the invention. In reference to FIGS. 1 and 5A, the system of FIG. 5A may be used as system 28 in FIG. 1 or alternatively be placed at dotted line position 29 in FIG. 1. Similar to the system of FIG. 2, a housing 32 is used for holding a reservoir 34 therein. Reservoir 34 holds a medium 36' which surrounds the holes 12d. Medium 36' may be a fluid or a gel. Medium 36' contains a substance or reagent which is to be introduced into the capillary 12. Capillary 12 is filled with a gel medium 62 which serves as the separation medium inside the capillary 12. The two ends of the capillary 12 may be placed in buffers as shown in FIG. 1 for carrying out the electrophoretic separation. A sample is injected into the gel medium 62 inside the capillary wall 12c. Under the influence of the electric field applied by high voltage source 20, the sample migrates in the gel medium from the inlet end 12a towards the location of the holes 12d. Different components of the sample may migrate at different electrophoretic mobilities, thereby causing the sample components to separate along the gel column as they migrate.

As noted above, medium 36' may be a fluid or a gel containing a substance or reagent which is to be introduced into the capillary. Since gravity or pressure may not be effective for introducing the substance through a gel medium inside the capillary, electrophoresis is used as the injection mechanism in the same manner as illustrated in reference to FIG. 3. To simplify the diagram, the voltage source 50 and electrode 54 have been omitted in FIG. 5A. The substance or reagent introduced from medium 36' through holes 12d into the gel medium 62 enhances the separation or detectability of the sample components. In reference to FIGS. 1, 5A, detector 22 is then used to detect the presence of the sample components in the same manner as described above. Thus, the structure of FIG. 5A may be used for on-column derivatization of analytes in gel-filled columns to enhance the separation or detection of the analytes.

FIG. 5B is a schematic view of a section of the separation capillary where the section includes the outlet end of the capillary and a system for introducing a substance into the separation capillary to illustrate a fourth embodiment of the invention. The embodiment of FIG. 5B differs from that of FIG. 5A only in that, in the case of FIG. 5B, capillary 12 is filled with gel only from the inlet end 12a to the location of the holes 12d instead of throughout the capillary tube. The section of the capillary 12 between holes 12d to the outlet end 12b is not filled with gel but is filled with an electrolyte buffer such as buffer 14 of FIG. 1. In FIG. 5B, reservoir 34 preferably contains a fluid medium which contains a substance or reagent which can be advantageously introduced into the capillary through holes 12d. In such event, the electrolyte buffer 14 will carry the sample components from holes 12d to the outlet end 12b of the capillary as the sample components migrate out of the gel 62.

The embodiment of FIG. 5B is advantageous over that of FIG. 5A in that a detector 64 may be placed between the holes 12d and the outlet 12b for detecting the contents of the gel to increase detection sensitivity while avoiding interferences caused by the presence of the gel. For this purpose, a detector 64 may be located within the capillary 12 downstream from hole 12d. For certain applications, the labelling reagent or substance may clog or other wise contaminate the gel in the column, so that the clogged or contaminated gel cannot be readily reused as a separation medium. In such event, the embodiment of FIG. 5B is advantageous over that of FIG. 5A since the labelling reagent or substance is introduced downstream from the gel, thereby reducing any clogging or contamination of the gel compared to FIG. 5A where the labelling reagent or substance must pass through the gel column.

In the embodiment of FIG. 5B, it is also possible to perform electrochemical detection in capillary gel separations. This may, for example, be performed by placing an electrochemical detector at or near the outlet end 12b of the capillary where the electrochemical detector is shown in two different dotted line positions 66' and 66" in FIG. 5B. As known to those skilled in the art, electrochemical detection is preferably performed at or near a reference potential such as ground potential so that the electrochemical detector should be placed at or near the outlet end 12b of the capillary and should not intrude too far into the high electric field inside capillary 12. Electrolyte buffer 14 would then carry the sample components as they exit the gel medium 62 towards electrochemical detector at 66' or 66".

While the invention has been illustrated above by reference to electrokinetic systems, the system is applicable to separation in chromatography as well. This is illustrated in FIG. 6. FIG. 6 is a schematic view of a capillary chromatographic system 10' to illustrate the invention. As shown in FIG. 6, instead of using an electrical means, the fluid in capillary 12 is moved by pressure generating devices such as pump P. The system for introducing a substance into the capillary 12 may be employed at solid line position 28, corresponding to a location upstream from detector 22. In the same manner as described above, the substance may be introduced into the capillary column inside tube 12 upstream from the detector at locations 28. The system for introducing a substance illustrated in FIGS. 1–3 is also applicable where the capillary is filled with a gel medium instead of a liquid medium.

In the above described embodiments, no side tube or tubes are necessary or desirable at the hole or holes 12d, so that it is unecessary to connect a side tube to the main separation column. The on-column junction of this invention for capillary columns is therefore much simpler to make than the above-described conventional connectors. At the junction, the substance or reagent present in the medium surrounding the hole is free to directly enter the separation column, without being restricted by any side tube.

While the invention has been described above by reference to various embodiments, it will be understood that various modifications and changes may be made without departing from the scope of the invention which is to be limited only by the appended claims.

What is claimed is:

1. An method for separating a sample into its components, employing a capillary tube defining a separation channel therein through which the sample travels and separates into its components, said tube having a side wall defining at least one hole therein, said hole extending through the side wall thereby permitting a fluid or particles to pass there through, said method comprising:

surrounding said hole with a fluid medium containing a substance so that the medium is dispersed in a region larger than size of the hole;

introducing a sample into the tube;

causing at least a portion of said sample to travel through the tube towards the location of the hole;

introducing said substance into the channel through the hole; and detecting the separated sample components at a location upstream or downstream from the hole.

2. The method of claim 1, wherein said substance introducing step includes applying pressure, gravity or electric potential differential between the channel and the medium.

3. The method of claim 1, further comprising the step of filling at least a portion of the tube with a stable phase medium before the sample and the substance are introduced into the tube.

4. The method of claim 3, wherein the filling step fills only the portion of the tube upstream from the hole but not beyond the hole or downstream from the hole.

5. The method of claim 4, said detecting step detects an electrochemical phenomenon.

6. The method of claim 5, said tube having an outlet downstream from the hole, wherein the detecting step is performed at or near the outlet.

7. The method of claim 1, said surrounding step being such that the medium contacts a portion of the side wall the tube adjacent to the hole.

8. The method of claim 7, said portion of said side wall forming a section of the tube, wherein said surrounding step includes filling at least a portion of a housing with said medium and immersing the section of the tube in the medium, so that the section is contained by the housing and the medium in said housing surrounds and contacts said section of the tube.

9. An apparatus for use in separating a sample into its components, comprising:

a capillary tube defining a separation channel therein through which the sample separates into its components, wherein one or more of said components travel in the tube defining an upstream and a downstream direction, said tube having a side wall defining at least one hole therein;

a medium dispersed in a region larger than size of the hole and surrounding said hole, said hole extending through the side wall thereby permitting a fluid or particles to pass between said channel and said medium, said medium containing a substance; and a first device introducing said substance into the channel through the hole.

10. The apparatus of claim 1, wherein said substance affects the speed of travel of the sample components.

11. The apparatus of claim 10, further comprising a detector adjacent to the separation channel detecting the separated sample components, said detector located upstream or downstream from the hole.

12. The apparatus of claim 1, said substance being a labelling reagent that affects the detectability of the components.

13. The apparatus of claim 1, wherein said substance enhances the separation of the sample components.

14. The apparatus of claim 9, further comprising a second device causing a sample in the channel to separate into components and to travel past said hole.

15. The apparatus of claim 14, said second device including a source applying an electric field in the channel.

16. The apparatus of claim 14, said detector including a source applying a pressure differential in the channel.

17. The apparatus of claim 9, wherein said first device including a source applying pressure, gravity or electric potential differential between the channel and the medium.

18. The apparatus of claim 1, further comprising a stable phase medium in the capillary tube.

19. The apparatus of claim 18, said stable phase medium located upstream from the hole.

20. The apparatus of claim 19, further comprising a detector adjacent to the separation channel detecting the separated sample components, said detecting means located downstream from the hole.

21. The apparatus of claim 20, wherein said detector is an electrochemical detector.

22. The apparatus of claim 21, said capillary tube having an outlet downstream from said hole, said detector located at or near said outlet.

23. The apparatus of claim 18, said stable phase medium located upstream and downstream from the hole.

24. The apparatus of claim 9, wherein said medium is a fluid medium.

25. The apparatus of claim 9, wherein said medium is a stable phase medium.

26. The apparatus of claim 25, wherein said stable phase medium is a gel.

27. The apparatus of claim 9, wherein said medium is in contact with a portion of the side wall of the tube adjacent to the hole.

28. The apparatus of claim 27, said apparatus further comprising a housing containing said medium and a section of said tube, said section including said portion of the side wall defining said at least one hole therein, so that the medium surrounds and is in contact with the side wall of said section of the tube.

29. An apparatus for use in separating a sample into its components, comprising:

a capillary tube defining a separation channel therein through which the sample separates into its components, wherein one or more of said components travel in the tube defining an upstream and a downstream direction, said tube having a side wall defining at least one hole therein;

a first medium surrounding said hole, said hole extending through the side wall thereby permitting a fluid or particles to pass between said channel and said first medium, said first medium containing a substance;

a second gel medium in the tube; and a first device introducing said substance into the channel through the hole.

* * * * *